United States Patent
Marcotte

(10) Patent No.: US 7,311,663 B2
(45) Date of Patent: Dec. 25, 2007

(54) MULTI-POSITIONABLE VAGINAL SPECULUM WITH REMOVABLE BLADES

(76) Inventor: Jacques R. Marcotte, 12805, rue du Parc, Mirabel (Québec) (CA) J7J 1P3

(*) Notice: Subject to any disclaimer, the term of this patent is extended or adjusted under 35 U.S.C. 154(b) by 898 days.

(21) Appl. No.: 10/642,742

(22) Filed: Aug. 19, 2003

(65) Prior Publication Data
US 2005/0043633 A1 Feb. 24, 2005

(51) Int. Cl.
*A61B 1/00* (2006.01)
*A61B 1/32* (2006.01)

(52) U.S. Cl. .............. 600/222; 600/225; 600/220

(58) Field of Classification Search ........ 600/184–220, 600/222, 225
See application file for complete search history.

(56) References Cited

U.S. PATENT DOCUMENTS

| | | | | |
|---|---|---|---|---|
| 2,544,932 A * | 3/1951 | Marco | ............ | 600/213 |
| 3,762,400 A * | 10/1973 | McDonald | ............ | 600/212 |
| 3,851,642 A | 12/1974 | McDonald | | |
| 3,890,961 A * | 6/1975 | Moore et al. | ............ | 600/222 |
| 5,231,973 A * | 8/1993 | Dickie | ............ | 600/222 |
| 5,499,964 A * | 3/1996 | Beck et al. | ............ | 600/220 |
| 5,509,893 A * | 4/1996 | Pracas | ............ | 600/224 |
| 6,048,308 A * | 4/2000 | Strong | ............ | 600/205 |
| 6,394,950 B1 * | 5/2002 | Weiss | ............ | 600/205 |
| 6,416,467 B1 * | 7/2002 | McMillin et al. | ............ | 600/224 |
| 6,589,168 B2 * | 7/2003 | Thompson | ............ | 600/221 |
| 6,702,740 B2 * | 3/2004 | Herold | ............ | 600/220 |
| 7,060,029 B1 * | 6/2006 | Hajianpour | ............ | 600/190 |
| 7,141,015 B2 * | 11/2006 | Ruane | ............ | 600/220 |
| 2002/0055670 A1 * | 5/2002 | Weiss | ............ | 600/220 |
| 2003/0176772 A1 * | 9/2003 | Yang | ............ | 600/220 |
| 2004/0225196 A1 * | 11/2004 | Ruane | ............ | 600/220 |

* cited by examiner

*Primary Examiner*—Cary E. O'Connor
*Assistant Examiner*—Jonathan Werner
(74) *Attorney, Agent, or Firm*—Ogilvy Renault LLP

(57) ABSTRACT

A speculum provides visual access to a body cavity, and such instrument is used by physicians for vaginal examination. The speculum comprises a handle having a frontal portion and a rear portion slidingly secured to the frontal portion. A blade angle positioner is pivotally connected by a pivot connection in a top end portion of the handle rear portion, whereby to angulate a top blade removably secured to a top blade connector anchor at a forward projecting end of the blade angle positioner. The handle frontal portion has a bottom blade connector anchor in a top forward end portion thereof. The top and bottom blades each have a connecting end provided with clamp connectors for removable engagement with a respective one of the top and bottom blade connector anchors. The blade angle positioner arrests the handle rear portion at a desired selected position by transfering a biasing force applied onto the blades when inserted into a body cavity and the blade connected to the blade angle positioner is in tension with cavity walls.

13 Claims, 4 Drawing Sheets

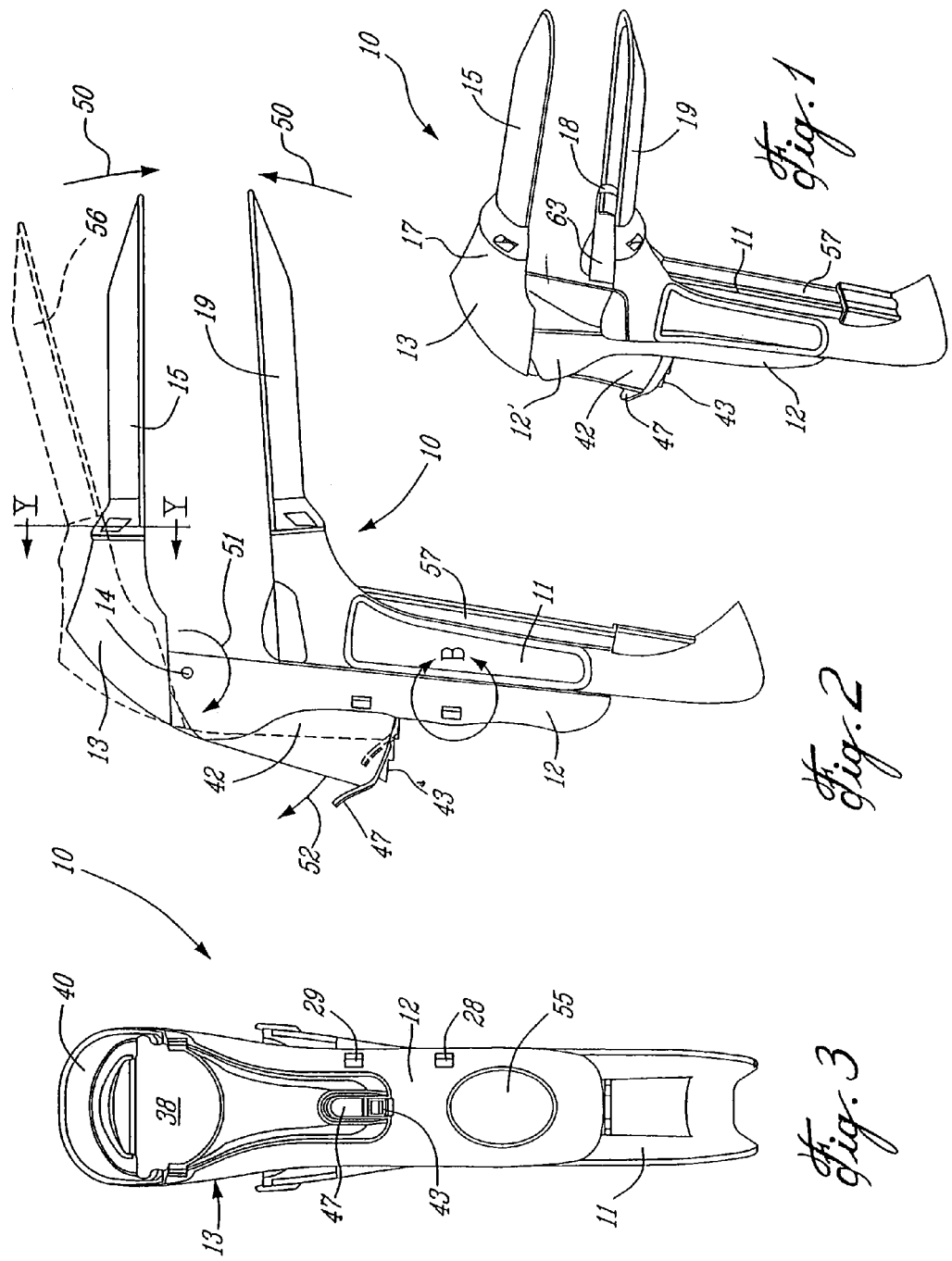

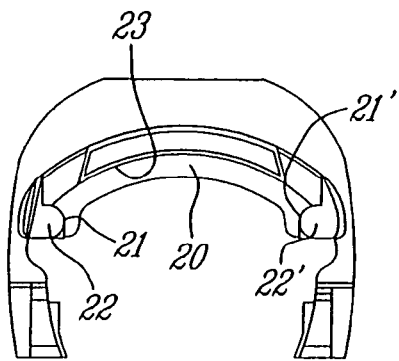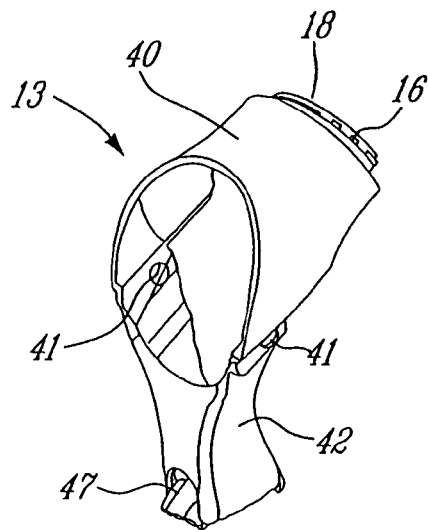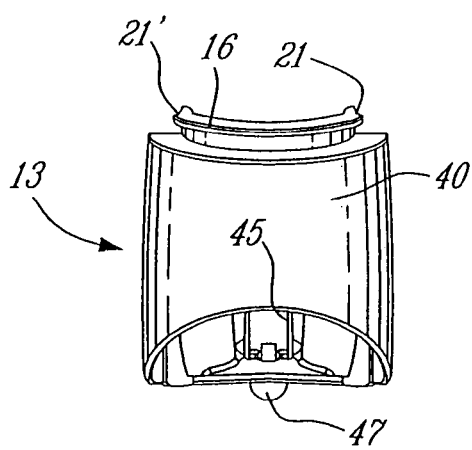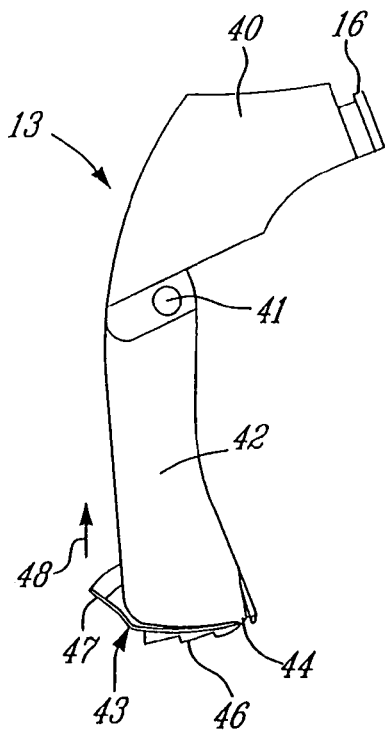
Fig. 5
Fig. 4A
Fig. 4C
Fig. 4B

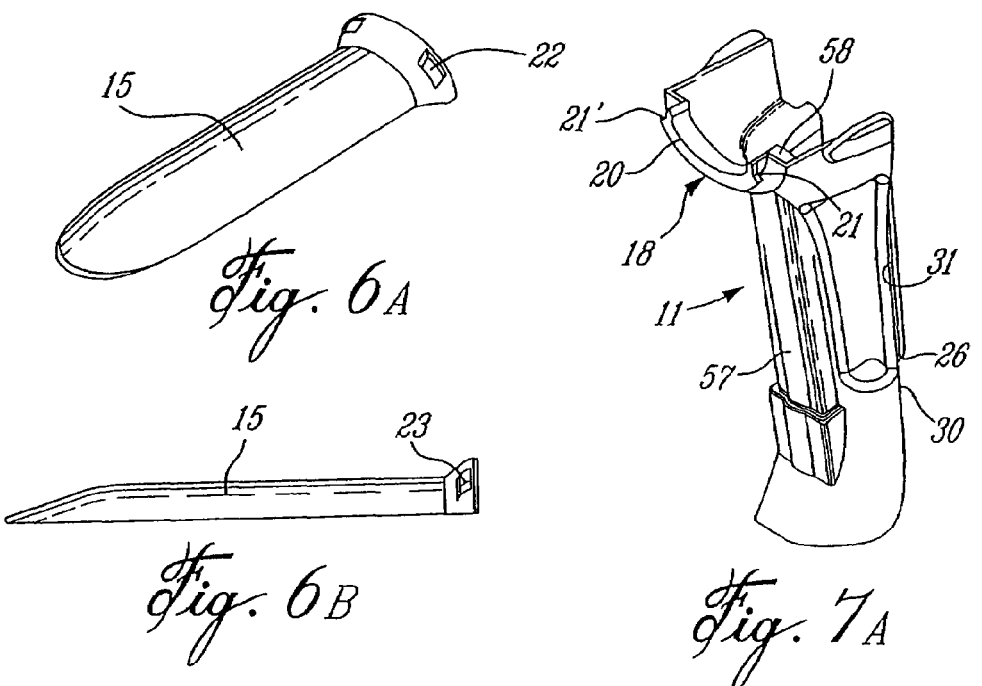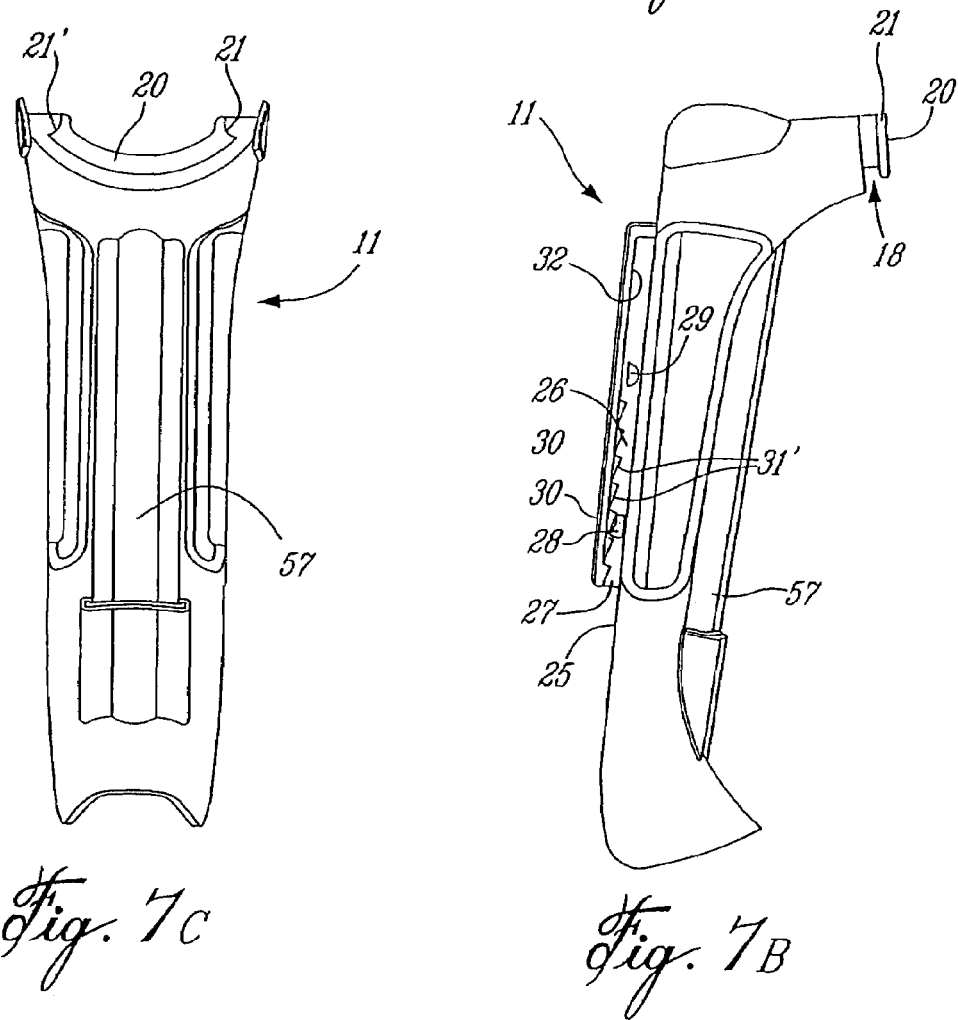

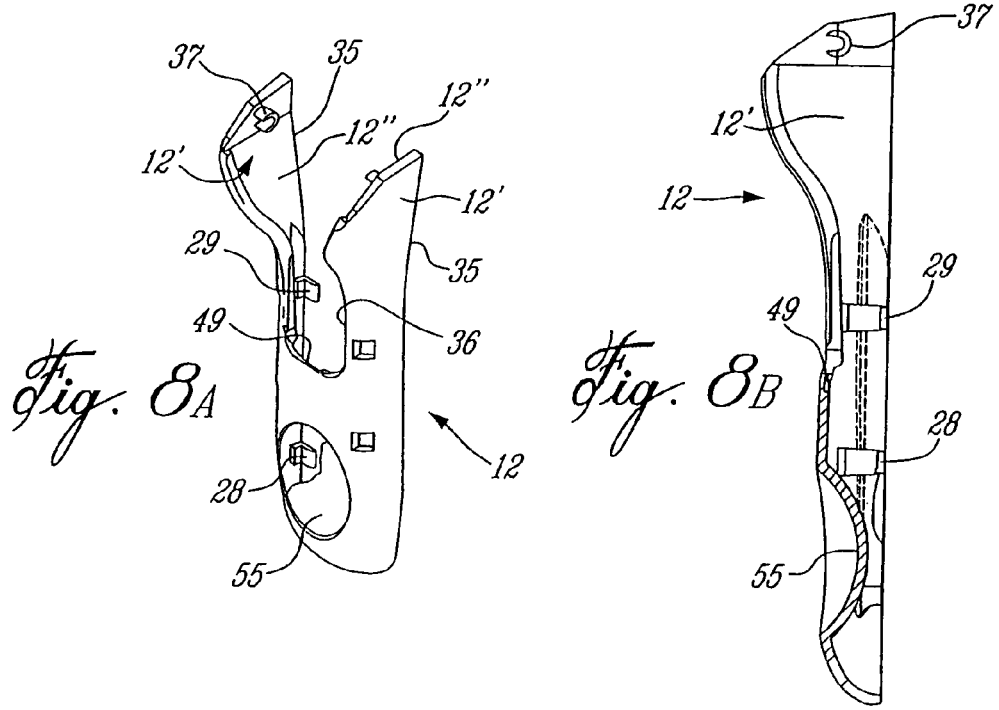
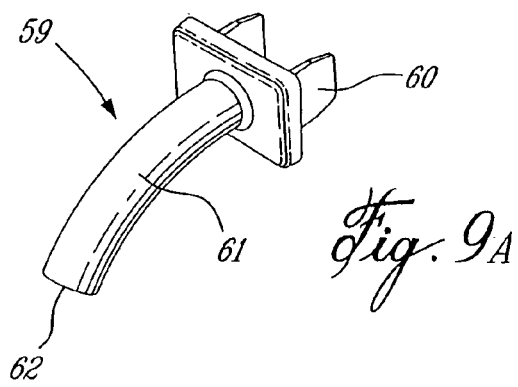
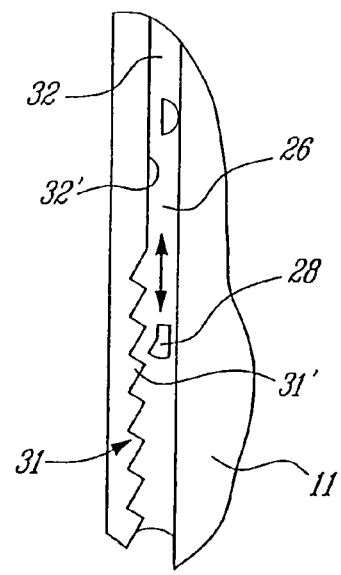

MULTI-POSITIONABLE VAGINAL SPECULUM WITH REMOVABLE BLADES

TECHNICAL FIELD

The present invention relates to a medical diagnostic instrument, and particularly to a speculum to provide visual access to a body cavity, such as a vaginal cavity.

BACKGROUND ART

A speculum is a diagnostic instrument used by physicians, and particularly gynecologists, for dilating the opening of the vaginal cavity in order that the interior may be more easily visible for observation. The speculum has two expandable blades that are inserted into the vagina in a closed condition and then expanded or moved apart for dilating the vaginal cavity. The speculum is usually a plastic molded instrument formed from a hard, clear and nontoxic plastic resin to be economically manufactured.

Most specula known provide adjustment of the blades from a retracted position to an open position, where the spatulas or blades are laterally displaced from one another. It is also desirable to angulate one of the spatulas or blades to create a larger internal opening. It is also known to provide specula with replaceable blades. Examples of such specula can be found, for example, in U.S. Pat. Nos. 3,762,400 and 3,851,642. These specula permit the blades to be disposed in different positions, and this is usually dependent on the comfort of the patient and the nature of the observation required by the physician. Known specula provide very few adjustments, and often this results in discomfort for the patient, as the speculum blades may apply excessive pressure to the walls of the body cavity, as well as being susceptible to causing pinching.

As previously described, it is also known to provide a speculum with interchangeable blades, as, for example, described in U.S. Pat. No. 3,762,400. However, these blades are attached on support members in such a way that they are not entirely sanitary, and it is essential to disinfect or sterilize these supports prior to mounting a displaceable blade thereover. Most known specula are of the type that are discarded after use, and this results in waste. A gynecologist can often use twenty of these instruments per day of work and, accordingly, there is excessive waste of plastics material, and this becomes costly to the physician. It also requires excessive storage space in his examination room. The consumption from private practice combined with hospital volume results in excessive plastic wastes. Such instrument which is discarded after use also represents higher costs to the end-user. In addition, it also requires more storage space while providers pay higher freight costs in view of the bulk packaging.

For years, specula have been made of metal and intended for longer procedures. Disinfection and/or sterilization have to be done; however, sterilization does not provide a full satisfactory efficiency in regard that all known infectious agents (eq. viruses) are not totally destroyed. Over recent years appeared plastic (disposable) specula which were of relatively inexpensive manufacturing.

Most recently, a general concern happened on the effects of discarding instruments in the environment. The present invention offers an economically manufacturing opportunity along with the combined effects form the metal and disposable specula: a more complete range of adjustments (angular and elevational) and a safe/efficient examination by discarding only the spatulas after use.

Spatulas as above referred are of a type that permits only rotary or arcuate relative movement of the spatulas (blades). As such, there is a pivotal or hinged connection provided between the two blades. In addition to this angular rotation of the blades, it is necessary that the blades be bodily adjustable relative to each other. Therefore, the instrument should not only permit substantial angular rotation of the blades but should also permit relative linear bodily adjustment.

SUMMARY OF INVENTION

It is a feature of the present invention to provide a speculum available in different sizes of lengths and width and wherein the blades are removably secured to the speculum by a simple clamping connection and wherein the handle assembly is reusable.

Another feature of the present invention is to provide a speculum having multi-positionable configurations to provide more comfort to the patients and to provide a greater range of adjustments of the speculum during an examination procedure. The reusable portion of the speculum (eq. handle) retains a fixed plastic component (eq. light pipe) which can be connected to conventional optical means to achieve a better visualization of the internal tissues.

A further feature of the invention relates therefore to the possibility to select among seven (7) elevations a combining effect of four (4) angular and/or linear positions.

According to the above features, from a broad aspect, the present invention provides a speculum to provide visual access to a body cavity. The speculum comprises a handle having a frontal portion and a rear portion slidingly secured to said frontal portion. A blade angle positioner is pivotally connected by a pivot connection in a top end portion of the handle rear portion whereby to angulate a top blade removably secured to a top blade connector anchor at a forward projecting end of the blade angle positioner. The handle frontal portion has a bottom blade connector anchor in a top forward end portion thereof. The top and bottom blades each have a connecting end provided with clamp connectors for removable engagement with a respective one of the top and bottom blade connector anchors. The blade angle positioner arrests the handle rear portion at a desired selected position by transferring a biasing force applied onto the blades when inserted into the body cavity and said blade connected to said blade angle positioner is placed in normal tension with cavity walls. The handle rear portion is retained in sliding fit in a guide slot formed in each of a pair of strait vertical side edges of the handle frontal portion. The guide slots each have a serrated section facing forwardly. The handle rear portion has a pair of transversely aligned serration-engaging teeth facing rearwardly and adapted to engage with a respective one of each serrated sections at a desire position therealong when the biasing force is a lied onto the blade. The blade angle positioner is provided with an integrally formed angle-selecting flexible ramp which is integrally molded therewith. The ramp has a series of teeth displaceable against a teeth-engaging edge of the handle rear portion when the angle positioner is displaced on the pivot connection.

BRIEF DESCRIPTION OF DRAWINGS

A preferred embodiment of the present invention will now be described with reference to the accompanying drawings in which:

FIG. 1 is a perspective view of a speculum constructed in accordance with the present invention;

FIG. 2 is a side view of the speculum;

FIG. 3 is a rear view of the speculum;

FIG. 4A is a perspective view of the blade angle positioner;

FIG. 4B is a side view of FIG. 4A;

FIG. 4C is a top view of FIG. 4B;

FIG. 5 is a cross-section view along section lines V-V of FIG. 2;

FIG. 6A is a perspective view of the detachable blade;

FIG. 6B is a side view of FIG. 6A;

FIG. 7A is a perspective view of the handle frontal portion;

FIG. 7B is a side view of FIG. 7A, illustrating the position of the guide slot;

FIG. 7C is a front view of FIG. 7B;

FIG. 8A is a perspective view of the rear sliding portion of the handle;

FIG. 8B is a sectional side view of FIG. 8A;

FIG. 8C is a fragmented section view showing the position of the serration-engaging teeth with respect to the serrated section of the guide slot and the position of the force transfer projecting finger relating thereto;

FIG. 9A is a perspective view of a removable light pipe; and

FIG. 9B is a top side view thereof.

DESCRIPTION OF PREFERRED EMBODIMENTS

Referring now to the drawings, and more particularly to FIGS. 1 to 3, there is shown generally at 10 the multi-positionable vaginal speculum of the present invention. The speculum as herein shown comprises a handle assembly formed by a handle frontal portion 11 and a sliding rear handle portion 12, which is detachably secured to the frontal portion 11. A blade angle positioner 13 is pivotally connected by a pivot connection 14 in a top end portion of the handle rear portion 12, whereby to angulate a top blade 15, which is removably secured to a connector anchor 16 (see FIGS. 4A to 4C) integrally formed at a forward projecting end 17 of the blade angle positioner 13.

The handle frontal portion 11 is also provided with a bottom blade connector anchor 18 to detachably secure the bottom blade 19 thereto.

With reference now to FIGS. 4A to 4C, and 7A to 7C, there is shown the construction of the blade connector anchors 16 and 18. In both cases, these anchors are identical in construction, and only one of these will be described with reference to FIGS. 7A and 7C. As herein shown, the connector anchor 18 is comprised of an arcuate guide ridge 20, having opposed locating cavities 21 and 21' at opposed ends of the ridge, whereby to receive in snap-fit clamping engagement therein the clamp connectors of the blades. As shown in the cross-section view of FIG. 5, these clamp connectors 22 and 22' are constituted by a pair of opposed inwardly facing shoulders, each disposed at an opposed end of an arcuate connector channel 23, forming an inner wall of the connecting end of the blades. The arcuate guide ridge 20 is received in close fit in the channel 23. The blades are connected by placing the arcuate ridge 20 with its locking cavity 21 in engagement with the clamping connector 22, and pressing the arcuate ridge 20 into the cavity 23 to permit the cavity 21' to snappingly engage with the clamp connector 22'. To disconnect the blades, they are merely twisted out of engagement. It is pointed out that the spatulas or blades are made of polystyrene and the handle components are constructed of polycarbonate. Both plastic resins are compatible with each other offering flexibility for the snap-fit clamping engagement of the blades. The transparency of the spatulas are important for diagnostic purposes. Among several advantages, they are non-toxic, light weight, resistant to pressure, compatible with most disinfecting agents and the handle can sustain sterilization.

Referring now to FIGS. 7A to 7C, there is shown the construction of the handle frontal portion 11, which is generally a U-shaped member defining opposed straight vertical side edges 25 rearwardly of the frontal portion. A guide slot 26 is formed in each of the vertical side edges 25, and has a bottom opening 27 to permit entry and displacement of a serration-engaging tooth 28 and a force transfer projecting finger 29 secured to the rear handle portion 12. The back wall 30 of the guide slot 26 is provided with a serrated section 31 disposed in a lower portion of the slot. The uppermost portion 32 is provided with a smooth inner wall. The serrations or teeth 31' of the serrated section 31 face forwardly of the frontal handle portion 11.

As shown in FIGS. 8A and 8B, the rear handle portion 12 is also of a substantially U-shaped cross-section, and it has a pair of these force transfer projecting fingers 29 projecting inwardly from a rear edge 35 thereof. The serration-engaging tooth 28 also projects from this rear edge 35, but in a lower portion of the rear handle portion 12. These elements 29 and 28 are positioned into the guide slot from the bottom opening 27 of the slot, and are free to move therealong as the rear handle portion slides up and down with respect to the guide slot. The rear handle portion 12 is maintained in engagement with the guide slot by the blade angle positioner 13, which is connected to the rear handle portion 12 via the pivot connection 14. Accordingly, the rear handle portion 12 is retained captive in the handle assembly by the blade angle positioner. To detach the component parts of the blade assembly, it is only necessary to flex the upper side walls 12' of the rear handle portion 12 to disconnect the pivot connections with the blade angle positioner. As shown in FIG. 8A, these upper portions or wings 12' can flex outwardly due to the large cut-out cavity 36 provided in the top portion of the rear handle portion 12. Pivot pin connectors 37 are located on the inside wall 12" of the upper wing portions 12'. The upper part of the cavity 36 provides for a sighting aperture 38, as shown in FIG. 3, whereby to provide visibility to a user person to the area between the blades.

Referring now to FIGS. 4A to 4C, the construction of the blade angle positioner 13 will be described. As herein shown, the top portion 40 of the blade angle positioner has a curvate wall, which, together with the cavity 36 in the rear handle portion, provides a large sighting aperture 38. Pivot pins 41 extend outwardly on a common transverse axis to be receivably connected within the connectors 37 of the rear handle portion. The lower extension portion 42 of the blade angle positioner is dimensioned to fit within the lower portion of the cavity 36 in the rear handle portion as illustrated in FIGS. 1 to 3.

As better shown in FIG. 4B, the lower extension portion 42 of the blade angle positioner 13 is provided with a flexible ramp 43, integrally molded therewith. The ramp 43 is connected at the front end portion 44 thereof to the lower extension portion 42 of the positioner. The ramp 43 is a narrow plastic strip 45, as shown in FIG. 4C, provided with a series of teeth 46 on an outer face thereof. The teeth 46 are integrally formed with the flexible ramp. The flexible ramp 43 also has a finger-engaging projection 47 at a free end thereof to displace the flexible ramp 46 inwardly of the lower extension portion 42, as indicated by arrow 48 in FIG. 4B, whereby to disconnect the teeth 46 from engagement with the lower engaging edge 49 of the cavity 36, as shown in FIG. 8A. There are four of the teeth 46 formed in the flexible ramp, which are biased outwardly against the engaging edge 49 of the rear handle portion.

Having thus described the components parts of the handle assembly and the connection of the removable blades to the handle assembly, and the angle positioner, the operation of the speculum will now be described.

When the speculum 10 is positioned in a body cavity, the top and bottom blades are in a closed condition, that is to say, the blades at the insertion are against each other. The closed blades are then inserted into the body cavity and with a slight rotation to allow the examination of the vaginal cavity through a 360 degree opening view, they then become separated as shown in FIGS. 1 to 3 by sliding the rear handle portion 12 upwardly with the serration-engaging tooth 25 moving upwardly over the serrated section 31 within the guide slot 26, as shown in FIG. 8C. Likewise, the force transfer projecting finger 29 moves upwardly until the blades are separated to a desired position. As the blades are separated apart, they are in contact with side walls of the cavity, and this places the blades in tension. Accordingly, a force is applied against the blades, as illustrated by arrows 50 in FIG. 2. This tension or force is transmitted along the top blade 15 to the pivot connection 14, urging the blade angle positioner 13 to exert a movement around the pivot pin 14, as indicated by arrow 51 in FIG. 2. This movement applies an outward force as indicated by arrow 52 on the lower portion of the positioner 13 below the pivot pin. Because the flexible ramp 43 is in toothed engagement with the engaging edge 49, this outward force, as indicated by arrow 52, is applied against the rear handle portion 12 due to the pulling action of the positioner. This causes the force transfer projecting finger 29 to move against the inner surface 32' of the upper portion 32 of the slot (see FIG. 8C), providing a pivot point to maintain the serration-engaging tooth 28 in engagement with an adjacent tooth 31' of the serrated section 31 formed in the rear wall 32' of the guide slot 26. Accordingly, the speculum component parts are all interconnected together at a desired position.

In order for the physician to displace the removable blades with respect to one another, there is provided on the rear wall of the rear handle portion 12 a thumb cavity 55, and, by depressing that cavity, the serration-engaging tooth 28 and the force transfer projecting fingers 29 are displaced rearwardly to disconnect from the inner surface 32' and the serrated section 31 of the slot 26. Thus, the rear handle portion 12 can be slid up or down to open or close the spacing between the blades 15 and 19. Once an ideal position has been reached, the thumb is removed from the thumb cavity. In order to angulate the top blade 15, all that is necessary is to exert an upward push on the tongue 47 to draw the flexible ramp 43 inwardly of the lower wall of the lower portion of the blade angle positioner 13, and to push the lower portion inwardly or to release it outwardly, causing the positioner to pivot on the pivot 14 to assume one of four desired open positions, one of which is illustrated at 56 in phantom line in FIG. 2.

As previously described, there are four teeth-engaging positions, and there are seven teeth 31' in the serrated section 31 of the guide slot. Accordingly, this provides to the physician with twenty-eight different positions or configuration possibilities of the speculum blades, whereby to achieve better placement of the blades to suit the comfort of a patient, or to provide better access to parts of the body cavity being inspected.

As shown in the drawings, and more specifically in FIGS. 1 to 3, and 7A to 7C, the frontal handle portion 11 is further provided with a light source channel 57. The channel has an open top end 58, configured to receive a removable light pipe 59, as illustrated in FIGS. 9A and 9B. As herein shown, the light pipe has a connector end 60, which fits into the open top end 58, and an angulated light-conducting solid plastic gooseneck 61, the free end 62 of which is positioned in the channel 63 (see FIG. 1) of the upper section of the handle frontal portion 11, whereby to direct a light beam between the blades 15 and 19. A light-dispersing dome 64 directs light from an optic fiber or other light conductor (not shown), and such a light pipe is well known in the art and is merely described as an accessory to the speculum of the present invention.

Because of the construction of the speculum 10, the handle assembly is reusable and only the blades are discarded. The handle portion is easy to assemble and compact. It provides multiple adjustments of the blades and improved visibility to a body cavity.

It is within the ambit of the present invention to cover any obvious modifications of the preferred embodiment described herein, provided such modifications fall within the scope of the appended claims.

I claim:

1. A speculum to provide visual access to a body cavity, said speculum comprising a handle having a frontal portion and a rear portion slidingly secured to said frontal portion, a blade angle positioner pivotally connected by a pivot connection in a top end portion of said handle rear portion whereby to angulate a top blade removably secured to a top blade connector anchor at a forward projecting end of said blade angle positioner, said handle frontal portion having a bottom blade connector anchor in a top forward end portion thereof, said top and bottom blades each having a connecting end provided with clamp connectors for removable engagement with a respective one of said top and bottom blade connector anchors, said blade angle positioner arresting said handle rear portion at a desired selected position by transferring a biasing force applied onto said blades when inserted into a body cavity and said blade connected to said blade angle positioner is placed in normal tension with cavity walls said handle rear portion being retained in sliding fit in a guide slot formed in each of a pair of straight vertical side edges of said handle frontal portion, said guide slots each having a serrated section facing forwardly, said handle rear portion having a pair of transversely aligned serration-engaging teeth facing rearwardly and adapted to engage with a respective one of each serrated sections at a desired position therealong when said biasing force is applied onto said blade and wherein said blade angle positioner is provided with an integrally formed angle-selecting flexible ramp integrally molded therewith, said ramp having a series of teeth displaceable against a teeth-engaging edge of said handle rear portion when said angle positioner is displaced on said pivot connection.

2. A speculum as claimed in claim 1, wherein said 1top and bottom blade connector anchors comprise an arcuate guide ridge having opposed locating cavities to receive in snap-fit clamping engagement therein said clamp connectors.

3. A speculum as claimed in claim 2, wherein said clamp connectors are constituted by a pair of opposed inwardly facing shoulders, each disposed at an opposed end of an arcuate connector channel formed in an inner wall of said connecting end of said blades, said arcuate guide ridge being received in close fit in said channel.

4. A speculum as claimed in claim 3, wherein said top and bottom blades are constructed of a suitable plastics material permitting flexibility for said snap-fit clamping engagement.

5. A speculum as claimed in claim 1, wherein said blade angle positioner is provided with a sighting aperture to permit visibility between said blades from a rear of said speculum.

6. A speculum as claimed in claim 1, wherein there are four teeth in said series of teeth, there being seven serrations in said serrated forwardly projecting section for engagement by said serration-engaging teeth, said four teeth and seven serrations permitting said blades to be displaced to one of twenty-eight different positions to permit a user person to achieve better placement of said blades to suit the comfort of a patient or provide better access to parts of said body cavity.

7. A speculum as claimed in claim 1, wherein said angle-selecting ramp is provided with a finger-engaging projection free end to displace said flexible ramp for disengaging said series of teeth with respect to said teeth-engaging edge of said handle rear portion to reposition said positioner.

8. A speculum as claimed in claim 1, wherein said handle rear portion is provided with means to disengage said serration-engaging tooth from said serrated section against said biasing force for sliding displacement of said handle rear portion.

9. A speculum as claimed in claim 8, wherein said serrated section has forwardly projecting serrations.

10. A speculum as claimed in claim 8, wherein said means to disengage is a thumb cavity formed integrally on a rear surface of said handle rear portion to provide for a user person to push said handle rear portion toward said frontal portion to disengage said serration-engaging teeth from said serrated section to permit said sliding displacement.

11. A speculum as claimed in claim 8, wherein said speculum is constructed of molded plastics parts, said handle frontal and rear portions and said blade angle positioner constituting a reusable handle assembly.

12. A speculum as claimed in claim 1, wherein said handle rear portion is also provided with a pair of transversely aligned force transfer projecting fingers which are positioned in a top portion of said guide slots to abut against a smooth wall section of said slots formed above said serrated section to provide a pivot for said handle rear portion to draw said serration-engaging teeth in engagement with their respective serrated sections.

13. A speculum as claimed in claim 1, wherein there is further provided a light source channel formed integrally with said handle frontal portion, said channel having an open top end configured to receive a removable light pipe therein for directing a light beam between said blades.

* * * * *